(12) United States Patent
Gamble et al.

(10) Patent No.: US 9,320,755 B2
(45) Date of Patent: Apr. 26, 2016

(54) THERAPEUTIC AND DIAGNOSTIC MOLECULES

(75) Inventors: Jennifer Gamble, Double Bay (AU); Mathew Vadas, Double Bay (AU); Gregory Goodall, Netherby (AU); Jennifer Young, Petersham (AU)

(73) Assignees: CENTENARY INSTITUTE OF CANCER MEDICINE AND CELL BIOLOGY, Camperdown (AU); UNIVERSITY OF SYDNEY, Sydney (AU); WENKART FOUNDATION, Leichardt (AU)

( * ) Notice: Subject to any disclaimer, the term of this patent is extended or adjusted under 35 U.S.C. 154(b) by 83 days.

(21) Appl. No.: 13/376,304

(22) PCT Filed: Jun. 4, 2010

(86) PCT No.: PCT/AU2010/000698
§ 371 (c)(1),
(2), (4) Date: Apr. 20, 2012

(87) PCT Pub. No.: WO2010/139026
PCT Pub. Date: Dec. 9, 2010

(65) Prior Publication Data
US 2012/0196925 A1 Aug. 2, 2012

(30) Foreign Application Priority Data
Jun. 5, 2009 (AU) .................................. 2009902615

(51) Int. Cl.
| C07H 21/02 | (2006.01) |
| C07H 21/04 | (2006.01) |
| C12N 15/63 | (2006.01) |
| C12N 15/79 | (2006.01) |
| C12N 15/113 | (2010.01) |
| A61K 31/7105 | (2006.01) |

(52) U.S. Cl.
CPC .......... *A61K 31/7105* (2013.01); *C12N 15/113* (2013.01); *C12N 2310/141* (2013.01); *C12N 2330/10* (2013.01); *G01N 2800/7014* (2013.01)

(58) Field of Classification Search
None
See application file for complete search history.

(56) References Cited

U.S. PATENT DOCUMENTS

| 2005/0261218 A1* | 11/2005 | Esau et al. ................ 514/44 |
| 2006/0185027 A1 | 8/2006 | Bartel |

FOREIGN PATENT DOCUMENTS

| WO | WO 2007/137342 | 12/2007 |
| WO | WO 2008/063318 | 5/2008 |
| WO | WO 2009/017803 | 2/2009 |

OTHER PUBLICATIONS

Young, et al. (2013) "Regulation of vascular leak and recovery from ischemic injury by general and VE-cadherin—restricted miRNA antagonists of miR-27," BLOOD, v.122(16):2911-9.*
Mertens-Talcott et al, The oncogenic micro-RNA-27a targets genes that regulate specificity protein transcription factors and the G2-M checkpoint in MDA-MB-231 breast cancer cells, Cancer Research, 67(22):11001-11 (Nov. 2007).
International Search Report dated Sep. 10, 2010 issued in corresponding International Patent Application No. PCT/AU2010/000698.
Written Opinion of the International Searching Authority dated Sep. 10, 2010 issued in corresponding International Patent Application No. PCT/AU2010/000698.
Bang, C. et al., "Cardiovascular importance of the microRNA-23/27/24 family,"Microcirculation, vol. 19, No. 3, Apr. 2012, pp. 208-214.
Biyashev, Dauren et al., "miR-27b controls venous specification and tip cell fate," Blood, vol. 119, No. 11, Mar. 2012, pp. 2679-2687.
European Patent Office, extended European search report and European search opinion for EP10782840, Oct. 9, 2013.
Kuehbacher, A. et al., "Role of dicer and drosha for endothelial microRNA expression and angiogenesis," Circulation Research, vol. 101, No. 1, Jul. 2007, pp. 59-68.
Kuehbacher, A. et al., "Targeting microRNA expression to regulate angiogenesis," Trends in Pharmaceutical Sciences, vol. 29, No. 1, Dec. 2007, pp. 12-15.
Jun, Ye et al., "miRNA-27b targets vascular endothelial growth factor C to inhibit tumor progression and angiogenesis in colorectal cancer," PLOS One, vol. 8, No. 4, Apr. 2013, p. e60687.
Melo, S.A. et al., "Angiogenesis is controlled by miR-27b associated with endothelial tip cells," Blood, vol. 119, No. 11, Mar. 2012, pp. 2439-2440.
Urbich, C. et al., "MicroRNA-27a/b controls endothelial cell repulsion and angiogenesis by targeting semaphorin 6A," Blood, vol. 119, No. 6, Feb. 2012, pp. 1607-1616.
Wang, Jie-Mei et al., "MicroRNA Mir-27b rescues impaired angiogenic function of endothelial progenitor cells and accelerates would healing in type 2 diabetes," Circulation, vol. 118, No. 18, Suppl. 2, Oct. 2008, p. S412.
Zhou, Q. et al., "Regulation of angiogenesis and choroidal neovascularization by members of microRNA-23 27 24 clusters," PNAS, vol. 108, No. 20, May 2011, pp. 8287-8292.

* cited by examiner

*Primary Examiner* — Jennifer McDonald
(74) *Attorney, Agent, or Firm* — Perkins Coie LLP

(57) ABSTRACT

The present invention relates to methods for modulating angiogenesis, comprising administering to a subject, or cells or tissue derived therefrom: (i) one or more miRNA, or precursors or variants thereof, wherein at least one of said miRNA comprises a seed region comprising the sequence UCACAGU (SEQ ID NO:37) to inhibit angiogenesis; or (ii) one or more antagonists of a miRNA, wherein said miRNA comprises a seed region comprising the sequence UCACAGU (SEQ ID NO:37) to promote or induce angiogenesis. Also provided are methods of diagnosis of conditions associated with abnormal angiogenesis, or determining predisposition thereto. Suitable pharmaceutical compositions are also provided.

9 Claims, 6 Drawing Sheets

A

B

C

THERAPEUTIC AND DIAGNOSTIC MOLECULES

CROSS-REFERENCE TO RELATED APPLICATIONS

This application is a national stage of International Patent Application No. PCT/AU2010/000698, filed Jun. 4, 2010, which claims the benefit of the priority of Australian Patent Application No. 2009902615, filed Jun. 5, 2009, which applications are incorporated herein by reference.

FIELD OF THE INVENTION

The present invention relates generally to microRNA species (miRNAs) downregulated during angiogenesis. The invention thereby relates to methods for the inhibition of angiogenesis and to methods for the promotion of angiogenesis by modulation of these miRNAs. The invention also relates to methods for the prevention and treatment of conditions characterised by, or associated with, abnormal angiogenesis. Further provided herein are miRNA expression signatures indicative of angiogenic processes, uses of miRNA disclosed herein as anti-angiogenic agents and in disease diagnosis, and uses of antagonists of miRNA disclosed herein as pro-angiogenic agents.

BACKGROUND OF THE INVENTION

Angiogenesis, the process by which new blood vessels are formed, is a fundamental process underlying many aspects of vertebrate growth and development including embryogenesis and fetal development. It is also crucial in ongoing physiological responses such as wound healing.

Angiogenesis is regulated by a complex combination of angiogenesis-stimulating growth factors and angiogenesis inhibitors. The balance between pro- and anti-angiogenic modulators governs when, where and to what extent angiogenesis occurs depending on the developmental state and/or physiological state of the organism. Misregulation of angiogenesis, leading to either excessive or insufficient vessel formation, can have significant consequences and is associated with a variety of pathological conditions. Excessive angiogenesis is associated with, for example, conditions such as cancer, chronic inflammatory conditions, ocular disorders and cardiovascular diseases. Similarly, inadequate angiogenesis is implicated in, for example, ischemic chronic wounds and some infertility.

In cancer, angiogenesis is crucial for the development of many cancers, for tumour growth and for metastasis. Tumours promote angiogenesis by the secretion of growth factors such as VEGF inducing blood vessel growth into the tumour. Blood vessel development provides the tumour with the required supply of nutrients and oxygen and a pathway for the elimination of waste products. Increased tumour vasculature then provides increased possibility for the tumour to metastasize. Anti-angiogenic therapy has recently emerged as a promising avenue for the treatment of cancer and may offer advantages over more traditional anti-cancer therapies, for example, the possibility of reduced susceptibility to the development of resistance. However, despite promise, there has to date been limited success in the development of efficacious anti-angiogenic agents and there remains a need for the identification of new targets and therapeutic molecules.

In view of the central role of normally regulated angiogenesis in development and numerous physiological processes, allied with the significant clinical consequences of abnormal angiogenesis (both up- and down-regulated), there is a clear need for the development of novel therapeutic options for, where required, the promotion of angiogenesis and for the inhibition of angiogenesis.

MicroRNAs (miRNAs) are an abundant class of highly conserved, small (typically 21-23 nucleotides) endogenous non-coding RNA molecules. miRNAs serve as post-transcriptional regulators of gene expression. They are crucial to many normal cellular functions, and play critical roles in, for example, cellular proliferation and differentiation, embryonic development, inflammation, immunity and many metabolic processes. Specific miRNAs, including expression patterns and altered regulation of expression of individual miRNAs, are also increasingly being implicated in a variety of disease conditions, including cancer and cardiovascular disease.

More than 1000 miRNAs have been identified to date, and more than 400 miRNAs with known sequence have been found in humans (see for example, http://microrna.sanger-ac.uk/sequences/index.shtml). Individual miRNA typically bind incompletely to their cognate target messenger RNA (mRNA) and as such each miRNA may bind to, and potentially regulate, many target mRNAs. Computational analysis suggests that there may be several hundred mRNA targets for any given miRNA. Accordingly, a unique miRNA may regulate the expression of one or more (potentially hundreds) different genes.

Mature miRNAs are derived from so-called pri-miRNAs that are transcribed from regions of non-coding DNA. Pri-miRNAs, usually containing several hundred nucleotides, are processed into stem-loop precursors (pre-miRNAs) of approximately 70 nucleotides by RNase III endonuclease. Pre-miRNAs are actively transported into the cytoplasm where they are further processed into short RNA duplexes, typically of 21-23 bp. The functional miRNA strand dissociates from its complementary non-functional strand and locates within the RNA-induced-silencing-complex (RISC). (Alternatively, RISC can directly load pre-miRNA hairpin structures.) miRNAs bind the 3'UTRs of target mRNAs and important in this binding is a so-called 'seed' region of approximately 6-7 nucleotides near the 5' end of the miRNA (typically nucleotide positions 2 to 8). The role of the 3' end is less clear. miRNA-induced regulation of gene expression is typically achieved by translational repression, either degrading proteins as they emerge from ribosomes or 'freezing' ribosomes, and/or promoting the movement of target mRNAs into sites of RNA destruction.

The present invention is predicated on the inventors' surprising finding that expression of a subset of miRNAs is downregulated during angiogenesis and that overexpression of such miRNA inhibits angiogenesis. Accordingly, the present invention opens avenues for the promotion or inhibition of angiogenesis and novel therapeutic approaches to the treatment of conditions associated with abnormal angiogenesis.

SUMMARY OF THE INVENTION

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The present invention provides, inter alia, methods for the promotion or inhibition of angiogenesis, said methods comprising regulating the level of expression of one or more miRNA, typically in endothelial cells, wherein altered regulation of a miRNA selected from miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*, relative to normal endogenous levels, is capable of promoting or inhibiting angiogenesis.

According to a first aspect of the present invention there is provided a method for inhibiting angiogenesis, the method comprising administering to a subject, or cells or tissue derived therefrom, one or more miRNA, or precursors or variants thereof, wherein at least one of said miRNA comprises a seed region comprising the sequence UCACAGU (SEQ ID NO:37).

In an embodiment the at least one miRNA comprising the seed region sequence UCACAGU is miR_27a or miR_27b. In a particular embodiment the at least one miRNA is miR_27a. The miRNA miR_27a may be hsa_miR_27a and may comprise the nucleotide sequence set forth in SEQ ID NO:1. The miRNA miR_27b may be hsa_miR_27b and may comprise the nucleotide sequence set forth in SEQ ID NO:2.

The subject may suffer from, be predisposed to, or otherwise at risk of developing a condition associated with excessive or unregulated angiogenesis.

The condition may be, for example, cancer, a cardiovascular disease, a chronic inflammatory disorder, an ocular disorder, endometriosis or adiposity. The cardiovascular disorder may be atherosclerosis or restenosis. The chronic inflammatory disorder may be rheumatoid arthritis, Crohn's disease or psoriasis. The ocular disorder may be retinopathy, diabetic retinopathy, glaucoma or macular degeneration. The macular degeneration may be age-related macular degeneration.

According to a second aspect there is provided a method for inhibiting angiogenesis, the method comprising administering to a subject, or cells or tissue derived therefrom, one or more miRNA, or precursors or variants thereof, wherein said miRNA is selected from miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*.

The miRNA may comprise a nucleotide sequence as set forth in any one of SEQ ID Nos:1 to 18.

According to a third aspect there is provided the use of a miRNA comprising a seed region comprising the sequence UCACAGU (SEQ ID NO:37), or a miRNA selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*, or a precursor or variant thereof, as an anti-angiogenic agent.

According to a fourth aspect there is provided the use of a miRNA comprising a seed region comprising the sequence UCACAGU (SEQ ID NO:37), or a miRNA selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*, or a precursor or variant thereof, for the manufacture of a medicament for the inhibition of angiogenesis.

Also provided herein are pharmaceutical compositions comprising one or more anti-angiogenic agents according to the third aspect, optionally together with pharmaceutically acceptable carriers, diluents and/or excipients.

According to a fifth aspect there is provided a method for promoting or inducing angiogenesis in cells or tissue of a subject, the method comprising administering to the subject, or cells or tissue derived therefrom, an effective amount of one or more antagonists of a miRNA, wherein said miRNA comprises a seed region comprising the sequence UCACAGU (SEQ ID NO:37).

In an embodiment the miRNA comprising the seed region sequence UCACAGU is miR_27a or miR_27b. In a particular embodiment the miRNA is miR_27a. The miRNA miR_27a may be hsa_miR_27a and may comprise the nucleotide sequence set forth in SEQ ID NO:1. The miRNA miR_27b may be hsa_miR_27b and may comprise the nucleotide sequence set forth in SEQ ID NO:2.

The antagonist may be an antisense oligonucleotide specific for the miRNA. The antisense oligonucleotide may comprise a nucleotide sequence as set forth in SEQ ID NO:19 or 20. The oligonucleotide sequence may comprise one or more modifications such as non-naturally occurring nucleotide analogues, non-phosphate linkages between nucleotides, and/or conjugated moieties.

The promotion or inducement of angiogenesis may be for wound repair, such as the healing of ischemic wounds. The promotion or inducement of angiogenesis may be for tissue repair, tissue regeneration or tissue engineering.

The subject may suffer from, be predisposed to, or otherwise at risk of developing a condition associated with impaired or suppressed angiogenesis. The condition may, for example, be coronary artery disease, stroke, a gynaecological disorder, infertility, or an ischemic wound.

According to a sixth aspect there is provided a method for promoting or inducing angiogenesis in cells or tissue of a subject, the method comprising administering to the subject, or cells or tissue derived therefrom, an effective amount of one or more antagonists of a miRNA selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*.

The miRNA may comprise a nucleotide sequence as set forth in any one of SEQ ID Nos:1 to 18.

The antagonist may be an antisense oligonucleotide specific for the miRNA. The antisense oligonucleotide may comprise a nucleotide sequence as set forth in any one of SEQ ID NOs:19 to 36.

According to a seventh aspect there is provided the use of an antagonist of a miRNA comprising a seed region comprising the sequence UCACAGU (SEQ ID NO:37) or of a miRNA selected from the group consisting of miR_27a, miR_27b, miR_23a, miR_23b, $miR_{20a}$, miR_21, miR_29a, miR_29b, miR_29c, miR_106a, miR_126, miR_193a, miR_195, miR_197, miR_221, miR_347 and miR_126*, as a pro-angiogenic agent.

According to an eighth aspect there is provided the use of an antagonist of a miRNA comprising a seed region comprising the sequence UCACAGU (SEQ ID NO:37) or of a miRNA selected from the group consisting of miR_27a, miR_27b, miR_23a, miR_23b, miR_20a, miR_29a, miR_29b, miR_29c, miR_106a, miR_126, miR_193a, miR_195, miR_197, miR_221, miR_347 and miR_126*, for the manufacture of a medicament for the promotion or inducement of angiogenesis.

Also provided herein are pharmaceutical compositions comprising one or more pro-angiogenic agents according to the seventh aspect, optionally together with pharmaceutically acceptable carriers, diluents and/or excipients.

According to a ninth aspect there is provided a method for diagnosing a disease or condition associated with abnormal angiogenesis in a subject, or determining the predisposition of a subject to such a disease or condition, the method comprising:
(a) obtaining a biological sample from the subject; and
(b) determining the level of expression of at least one miRNA, or a precursor or variant thereof in the sample, the miRNA
   (i) comprising a seed region comprising the sequence UCACAGU (SEQ ID NO:37), or
   (ii) being selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*,
wherein the level of expression of the at least one miRNA is indicative of a disease or condition associated with abnormal angiogenesis, or a predisposition thereto, in the subject.

According to a tenth aspect there is provided the use of a miRNA comprising a seed region comprising the sequence UCACAGU (SEQ ID NO:37) or of a miRNA selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126* for the detection of molecules bound by or regulated by said miRNA, wherein the activity or expression of said molecules is associated with angiogenesis.

BRIEF DESCRIPTION OF THE DRAWINGS

The present invention will now be described, by way of non-limiting example only, with reference to the accompanying drawings.

FIG. 3. Overexpression of hsa_miR_27a disrupts in vitro tube formation. HUVEC were transfected with either a pre-miR negative control (A) or with a precursor for hsa_miR_27a which allowed its overexpression (B). 24 h post transfection cells were plated onto Matrigel™ and observed over a 24 h time period. Areas where tubes were not able to join and make a stable network are indicated with white arrows. Very thin tubes are indicated by black arrows. (C) Number of capillary tubes formed per field of view quantified. Results shown are the mean of four independent HUVEC lines ±SEM. *, $p<0.05$ control vs miR_27a.

Figure 1A:
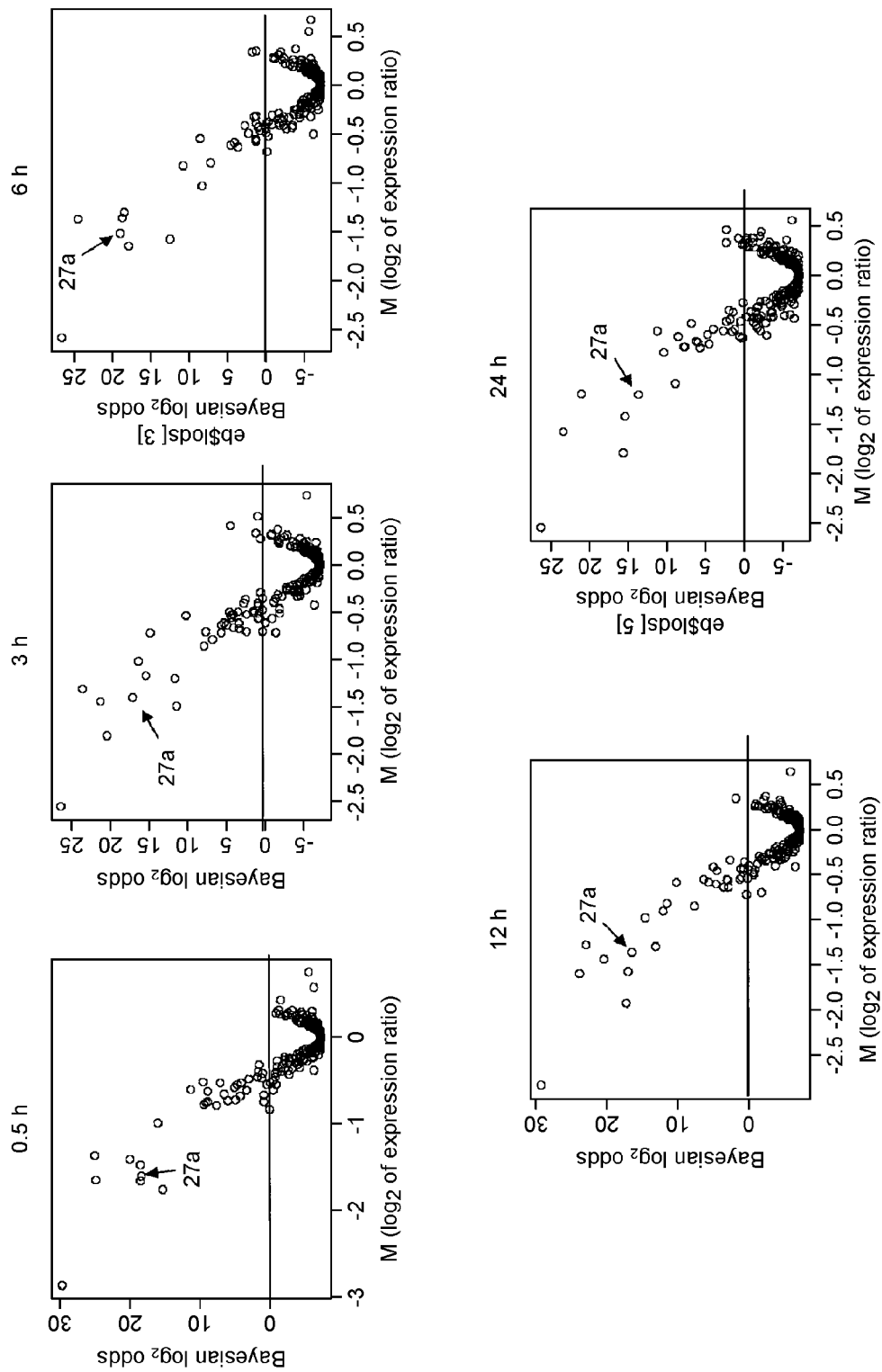
FIG. 1. Identification of microRNAs that are regulated during in vitro angiogenesis. A. Volcano plots showing changes in microRNAs detected by microarray of RNA isolated human umbilical vein endothelial cells (HUVEC) from timepoints associated with significant angiogenic events. Bayesian log odds of differential expression is plotted against log 2 (expression at timepoint divided by expression at time zero). B. Quantification of hsa_miR_27a expression levels as measured by Taqman real-time PCR are shown. HUVEC were harvested and either lysed (t-0 unstim) or stimulated with PMA and AC11 and lysed (t-0 stim) or were replated after PMA and AC11 stimulation onto a 3D collagen gel for either 15 or 30 minutes. Data represents the mean of triplicate PCR assays ±s.e.m. Results shown are normalized to snoU6B.3 lines of endothelial cells (EC).

The nucleotide sequences of miRNA disclosed herein are set forth in SEQ ID NOs:1 to 18. Nucleotide sequences of exemplary antisense oligonucleotides complementary to the miRNA sequences of SEQ ID NOs: 1 to 18 are set forth in SEQ ID NOs:19 to 36. The sequence representing the miRNA seed region of miR_27a and miR_27b is set forth in SEQ ID NO:37.

DETAILED DESCRIPTION OF THE INVENTION

The term "abnormal" when used herein in relation to angiogenesis means angiogenesis that is undesirable or inappropriately regulated. Thus abnormal angiogenesis may be upregulated or excessive with respect to normally regulated angiogenesis, or alternatively may be down-regulated, impaired or suppressed with respect to normally regulated angiogenesis. In each case the alteration or abnormality in angiogenesis may be quantitative, temporal and/or spatial. That is, in the case of upregulated or excessive angiogenesis for example, angiogenesis may occur at an abnormally high level, occur at a time when angiogenesis would normally not occur, and/or occur in a tissue or location where angiogenesis would normally not occur. Similarly, in the case of impaired or suppressed angiogenesis, a tissue or a body's ability to induce or initiate angiogenesis may be impaired such that angiogenesis cannot occur at sufficient levels, and/or occur in the required circumstances (time and/or location) to maintain a normal healthy state.

In the context of this specification, the term "activity" as it pertains to a protein, polypeptide or polynucleotide means any cellular function, action, effect or influence exerted by the protein, polypeptide or polynucleotide, either by a nucleic acid sequence or fragment thereof, or by the protein or polypeptide itself or any fragment thereof.

In the context of this specification, the term "antagonist" refers to any agent capable of blocking or inhibiting the expression and/or activity of a miRNA molecule. Thus, the antagonist may operate to prevent transcription or post-transcriptional processing of the miRNA or otherwise inhibit the activity of the miRNA in any way, via either direct or indirect action. The antagonist may for example be nucleic acid, peptide, any other suitable chemical compound or molecule or any combination of these. Additionally, it will be understood that in indirectly impairing the activity of the miRNA, the antagonist may effect the activity of other cellular molecules which may in turn act as regulators of the expression of activity of the miRNA itself. Similarly, the antagonist may effect the activity of molecules which are themselves subject to regulation or modulation by the miRNA.

As used herein the term "associated with" when used in the context of a disease or condition "associated with" abnormal angiogenesis means that the disease or condition may result from, result in, be characterised by, or otherwise associated with the abnormal angiogenesis. Thus, the association between the disease or condition and the abnormal angiogenesis may be direct or indirect and may be temporally separated.

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

It will be understood that as used herein the term "expression" may refer to expression of a polypeptide or protein, or to expression of a polynucleotide or gene, depending on the context. The polynucleotide may be coding or non-coding (e.g. miRNA). Expression of a polynucleotide may be determined, for example, by measuring the production of RNA transcript levels. Expression of a protein or polypeptide may be determined, for example, by immunoassay using an antibody(ies) that bind with the polypeptide.

As used herein the term "miRNA species" refers to a microRNA of a specific nucleotide sequence. The terms "miRNA species", "miRNA" and "miRNA molecule" may be used interchangeably herein. Those skilled in the art will recognise that reference to a miRNA or a miRNA molecule does not mean a single (numerical) molecule, but rather a single type or species of molecule.

As used herein the term "oligonucleotide" refers to a single-stranded sequence of ribonucleotide or deoxyribonucleotide bases, known analogues of natural nucleotides, or mixtures thereof. An "oligonucleotide" comprises a nucleic-acid based molecule including DNA, RNA, PNA, LNA or any combination thereof. An oligonucleotide that predominantly comprises ribonucleotide bases, natural or non-natural, may be referred to as an RNA oligonucleotide. Oligonucleotides are typically short (for example less than 50 nucleotides in length) sequences that may be prepared by any suitable method, including, for example, direct chemical synthesis or cloning and restriction of appropriate sequences. "Antisense oligonucleotides" are oligonucleotides complementary to a specific DNA or RNA sequence. Typically in the context of the present invention an antisense oligonucleotide is an RNA oligonucleotide complementary to a specific miRNA. The antisense oligonucleotide binds to and silences or represses, partially of fully, the activity of its complementary miRNA. Not all bases in an antisense oligonucleotide need be complementary to the 'target' or miRNA sequence; the oligonucleotide need only contain sufficient complementary bases to enable the oligonucleotide to recognise the target. An oligonucleotide may also include additional bases. The antisense oligonucleotide sequence may be an unmodified ribonucleotide sequence or may be chemically modified or conjugated by a variety of means as described herein.

The term "polynucleotide" as used herein refers to a single- or double-stranded polymer of deoxyribonucleotide, ribonucleotide bases or known analogues of natural nucleotides, or mixtures thereof. A "polynucleotide" comprises a nucleic-acid based molecule including DNA, RNA, PNA, LNA or any combination thereof. The term includes reference to the specified sequence as well as to the sequence complimentary thereto, unless otherwise indicated. Polynucleotides may be chemically modified by a variety of means known to those skilled in the art. Thus a "polynucleotide" comprises a nucleic-acid based molecule including DNA, RNA, PNA, LNA or any combination thereof.

The term "subject" as used herein refers to mammals and includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Preferably, the mammal is human or a laboratory test animal. Even more preferably, the mammal is a human.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. In conditions which display or a characterized by multiple symptoms, the treatment or prevention need not necessarily remedy, prevent, hinder, retard, or reverse all of said symptoms, but may prevent, hinder, retard, or reverse one or more of said symptoms.

As exemplified herein, the inventors have determined that the level of expression of a group of specific miRNAs is rapidly and significantly downregulated upon inducement of angiogenic conditions in cell culture. Overexpression of at least one of these miRNA is demonstrated herein to inhibit blood vessel formation. The findings described herein offer new therapeutic targets for the modulation of angiogenesis and avenues for the treatment, prevention and diagnosis of diseases and conditions associated with abnormal angiogenesis.

The miRNA described herein as downregulated during angiogenesis include: miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*.

In particular aspects the present invention provides methods and agents for the inhibition of angiogenesis and for the treatment or prevention of conditions associated with excessive or unregulated angiogenesis. The methods may comprise the administration of one or more miRNA, at least one of which comprises a seed region comprising the sequence UCACAGU (SEQ ID NO:37), or one or more miRNA selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*, or precursors or variants thereof.

Administration may be directly to a subject in need of treatment, or may be ex vivo administration to cells or tissue derived from the subject. The miRNAs to be administered may be synthetically produced or naturally derived from a cellular source. Typically the miRNA may be derived from the species of the subject to be treated, or constitute a sequence identical to miRNA from that species. Thus, typically where the subject is a human the miRNA will be human-derived miRNA sequences.

Embodiments disclosed herein contemplate the administration of mature miRNA, precursors or variants thereof, or agents capable of modulating the expression or activity of said miRNA. Precursors include pri-miRNA and pre-miRNA molecules that can be processed into the mature active miRNA intracellularly. Variants include nucleotide sequences that are substantially similar to sequences of miRNA disclosed herein. Typically variant sequences will possess qualitative biological activity in common. Variants may comprise altered residues at one or more locations and may share, for example, 90%, 91%, 92%, 93%, 94%, 95%, 96%, 97%, 98% or 99% sequence identity. Alternatively or in addition variants may comprise modifications, such as non-natural residues at one or more positions.

The nucleotide sequences of the human (hsa) and rat (mo) miRNA disclosed herein are shown in SEQ ID NOs:1 to 18. The correspondence between miRNA designation and SEQ ID NO. is given in Table 2 in Example 1. Additional sequence information for these miRNA, including genomic location, can be found at http://microrna.sanger.ac.uk/sequences/index.shtml.

The invention also provides antagonists of these miRNA and uses thereof. In particular aspects the present invention provides methods and agents for the promotion of angiogenesis and for the treatment or prevention of conditions associated with impaired or suppressed angiogenesis. The methods may comprise the administration of antagonists of one or more miRNA, at least one of which miRNA comprises a seed region comprising the sequence UCACAGU (SEQ ID NO:37), or wherein the miRNA is selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*.

Those skilled in the art will readily appreciate that suitable antagonists for use in accordance with embodiments disclosed herein may take a variety of forms. The antagonist may be an antisense construct comprising a nucleotide sequence specific to an miRNA of the invention, or a portion thereof, wherein the antisense construct inhibits, at least partially, the expression or activity of the miRNA. By "specific" it is meant that the antisense construct is substantially specific for the miRNA, but not necessarily exclusively so. That is, while being specific for a particular miRNA sequence, the antisense construct may also cross-hybridise with other sequences, such as other miRNA sufficient to inhibit expression. Further, for example, the nucleotide sequence of an antisense construct according to the present invention may display less than 100% sequence identity with a particular miRNA and retain specificity thereto. It will be appreciated by those skilled in the art that suitable antisense constructs need not bind directly with the miRNA to which they are directed in order to effect the expression or activity of those miRNA. Binding of an antisense construct to its complementary cellular nucleotide sequence may interfere with transcription, RNA processing, transport, and/or stability of the miRNA to which it is specific. An antisense molecule may comprise DNA, RNA, LNA, PNA or any combination thereof.

Suitable antisense constructs for use in accordance with embodiments disclosed herein include, for example, antisense oligonucleotides, small interfering RNAs (siRNAs) and catalytic antisense nucleic acid constructs. Suitable antisense oligonucleotides may be prepared by methods well known to those of skill in the art. Typically oligonucleotides will be chemically synthesized on automated synthesizers. By way of non-limiting example, the sequences of particular antisense oligonucleotides specific for miRNA disclosed herein are shown in SEQ ID Nos: 19 to 36. The miRNA to which these oligonucleotides are specific are indicated in Table 1 below.

TABLE 1

SEQ ID NOs for miRNA disclosed herein and corresponding exemplary antisense oligonucleotides.

| SEQ ID NO | |
|---|---|
| miRNA | Antisense oligo |
| 1 | 19 |
| 2 | 20 |
| 3 | 21 |
| 4 | 22 |
| 5 | 23 |
| 6 | 24 |
| 7 | 25 |
| 8 | 26 |
| 9 | 27 |
| 10 | 28 |
| 11 | 29 |
| 12 | 30 |
| 13 | 31 |
| 14 | 32 |
| 15 | 33 |
| 16 | 34 |
| 17 | 35 |
| 18 | 36 |

These exemplary oligonucleotides are 100% complementary to their respective miRNAs, although those skilled in the art will readily appreciate that one or more base changes may be made such that less than 100% complementarity exists whilst the oligonucleotide retains specificity for its miRNA and retains antagonistic activity against this miRNA. Further, as described below, oligonucleotide sequences may include one or more chemical modifications without departing from the scope of the present invention.

Oligonucleotides in accordance with the invention may include modifications designed to improve their delivery into cells, their stability once inside a cell, and/or their binding to the appropriate miRNA target. For example, the oligonucleotide sequence may be modified by the addition of one or more phosphorothioate (for example phosphoromonothioate or phosphorodithioate) linkages between residues in the sequence, or the inclusion of one or morpholine rings into the backbone. Alternative non-phosphate linkages between residues include phosphonate, hydroxylamine, hydroxylhydrazinyl, amide and carbamate linkages (see, for example, United States Patent Application Publication No. 20060287260, Manoharan I., the disclosure of which is incorporated herein in its entirety), methylphosphonates, phosphorothiolates, phosphoramidates or boron derivatives. The nucleotide residues present in the oligonucleotide may be naturally occurring nucleotides or may be modified nucleotides. Suitable modified nucleotides include 2'-O-methyl nucleotides, such as 2'-O-methyl adenine, 2'-O-methyl-uracil, 2'-O-methyl-thymine, 2'-O-methyl-cytosine, 2'-O-methyl-guanine, 2'-O-methyl-2-amino-adenine; 2-amino-adenine, 2-amino-purine, inosine; propynyl nucleotides such as 5-propynyl uracil and 5-propynyl cytosine; 2-thio-thymidine; universal bases such as 5-nitro-indole; locked nucleic acid (LNA), and peptide nucleic acid (PNA). The ribose sugar moiety that occurs naturally in ribonucleosides may be replaced, for example with a hexose sugar, polycyclic heteroalkyl ring, or cyclohexenyl group as described in United States Patent Application Publication No. 20060035254, Manoharan et al., the disclosure of which is incorporated herein in its entirety. Alternatively, or in addition, the oligonucleotide sequence may be conjugated to one or more suitable chemical moieties at one or both ends. For example, the oligonucleotide may be conjugated to cholesterol via a suitable linkage such as a hydroxyprolinol linkage at the 3' end.

The synthesis of modified oligonucleotides with 'silencing' activity against specific miRNA ("antagomirs") is described in Krutzfeldt, J. et al., 2005, Nature 438:685-689, the disclosure of which is incorporated herein in its entirety. For example, Krutzfeldt et al. discloses the sequences of antagomirs comprising 2-O-methyl nucleotides, phosphorothioate linkages between residues at the 5' and 3' end, and a conjugated cholesterol moiety via a hydroxyprolinol linkage at the 3' end. Embodiments as disclosed herein contemplate use of antagomirs modified in the manner described in Krutzfeldt et al. as well as modifications or variations thereof. The design of oligonucleotides or antagomirs for use in accordance with embodiments disclosed herein is well within the capabilities of those skilled in the art.

An alternative antisense technology, known as RNA interference (RNAi), see, eg. Chuang et al. (2000) *PNAS USA* 97: 4985) may be used, according to known methods in the art (for example Fire et al. (1998) *Nature* 391: 806-811; Hammond, et al. (2001) *Nature Rev, Genet.* 2: 110-1119; Hammond et al. (2000) *Nature* 404: 293-296; Bernstein et al. (2001) *Nature* 409: 363-366; Elbashir et al (2001) *Nature* 411: 494-498; WO 99/49029 and WO 01/70949, the disclosures of which are incorporated herein by reference), to inhibit the expression or activity of miRNA. RNAi refers to a means of selective post-transcriptional gene silencing by destruction of specific RNA by small interfering RNA molecules (siRNA). The siRNA is generated by cleavage of double stranded RNA, where one strand is identical to the message to be inactivated. Double-stranded RNA molecules may be synthesised in which one strand is identical to a specific region of the miRNA transcript and introduced directly. Alternatively corresponding dsDNA can be employed, which, once presented intracellularly is converted into dsRNA. Methods for the synthesis of suitable molecules for use in RNAi and for achieving post-transcriptional gene silencing are known to those of skill in the art.

A further means of inhibiting the expression or activity of miRNA to which the invention relates may be achieved by introducing catalytic antisense nucleic acid constructs, such as DNAzymes and ribozymes, which are capable of cleaving miRNA transcripts. Ribozymes, for example, are targeted to, and anneal with, a particular sequence by virtue of two regions of sequence complementarity to the target flanking the ribozyme catalytic site. After binding the ribozyme cleaves the target in a site-specific manner. The design and testing of ribozymes which specifically recognise and cleave miRNA sequences can be achieved by techniques well known to those in the art (for example Lieber and Strauss, (1995) *Mol. Cell. Biol.* 15:540-551, the disclosure of which is incorporated herein by reference).

It will also be recognised by those skilled in the art that an antagonist in accordance with embodiments of the invention may effect a modulator or regulator of the expression or activity of a miRNA disclosed herein. Similarly, the antagonist may effect a target of a miRNA disclosed herein. Thus, antagonists may take any suitable form, depending on the nature and identity of the molecule(s) to be effected, such as for example a small molecule inhibitor, peptide inhibitor or antibody.

Embodiments of the present invention relate to methods and compositions for the treatment of diseases and conditions associated with abnormal angiogenesis, as defined herein. Abnormal angiogenesis may be excessive or unregulated, or may be impaired or suppressed. Thus such treatments are typically designed to modulate angiogenesis so as to normalise the level, time and/or location of angiogenesis and thereby treat or retard the progression of the disease or condition. Embodiments of the invention also contemplate methods for the prevention of diseases and conditions associated with abnormal angiogenesis, typically in a subject predisposed to such a disease or condition, or otherwise at risk of developing such a disease or condition.

Those skilled in the art will readily appreciate the full scope of diseases and conditions that may be associated with abnormal angiogenesis and to which embodiments of the invention may be directed. By way of non-limiting example, diseases and conditions associated with excessive or upregulated angiogenesis, and thus where inhibition of angiogenesis in accordance with embodiments of the invention may be desired, include cancer (solid and hematologic tumours), cardiovascular diseases, such as atherosclerosis and restenosis, chronic inflammatory disorders, such as rheumatoid arthritis and Crohn's disease, ocular disorders such as retinopathy, diabetic retinopathy, glaucoma and macular degeneration (including age-related macular degeneration), endometriosis, psoriasis and adiposity. Similarly by way of non-limiting example, circumstances where the promotion of angiogenesis in accordance with embodiments of the invention may be desired, include in wound healing, such as the treatment of ischemic wounds, in the treatment of some gynaecological disorders and infertility, in the treatment of coronary artery disease, in the prevention of stroke, in tissue repair or regeneration, and tissue engineering. In the case of tissue engineering the generation of large tissue volumes requires rapid vascularisation of three-dimensional scaffold constructs. The role of miR_27a in angiogenesis in a three-dimensional milieu, as exemplified herein, suggests the potential application of the inhibition of miRNA such as miR_27a in promoting angiogenesis in tissue engineering scaffolds.

According to embodiments of the invention, miRNA and antagonists thereof administered to achieve inhibition or promotion of angiogenesis may be administered in any suitable form. Typically these will be administered as pharmaceutical compositions, which compositions may comprise one or more pharmaceutically acceptable carriers, excipients or diluents. Such compositions may be administered in any convenient or suitable route such as by parenteral, oral, nasal or topical routes. Thus compositions may be formulated in a variety of forms suitable for the chosen route of administration, for example as capsules, tablets, caplets, elixirs for oral ingestion, in an aerosol form suitable for administration by inhalation (such as by intranasal inhalation or oral inhalation), ointment, cream or lotion suitable for topical administration, or in an injectable formulation suitable for parenteral administration, such as subcutaneous, intramuscular or intravenous injection. The preferred route of administration will depend on a number of factors including the condition to be treated and the desired outcome. The most advantageous route for any given circumstance can be determined by those skilled in the art.

It will be understood that the specific dose level of a composition for any particular individual will depend upon a variety of factors including, for example, the activity of the specific agents employed, the age, body weight, general health and diet of the individual to be treated, the time of administration, rate of excretion, and combination with any other treatment or therapy. Single or multiple administrations can be carried out with dose levels and pattern being selected by the treating physician.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for parenteral administration, or in the form of a formulation suitable for oral ingestion (such as capsules, tablets, caplets, elixirs, for example).

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colorings agents. When used in capsule form the capsules may be coated with compounds such as glyceryl monostearate or glyceryl distearate which delay disintegration. Adjuvants typically include emollients, emulsifiers, thickening agents, preservatives, bactericides and buffering agents. For administration as an injectable solution or suspension, non-toxic parenterally acceptable diluents or carriers can include, Ringer's solution, isotonic saline, phosphate buffered saline, ethanol and 1,2 propylene glycol.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, *Remington's Pharmaceutical Science,* 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as siliceous silicas, and other ingredients such as lanolin, may also be included.

miRNA and antagonists thereof may be administered in accordance with embodiments of the invention as liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolizable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference. The agents may also be administered in the form of microparticles. For example, biodegradable microparticles formed from polylactide (PLA), polylactide-co-glycolide (PLGA), and epsilon-caprolactone (ε-caprolactone) may be used.

The invention also contemplates encapsulated formulations to protect polynucleotide and oligonucleotide agents against rapid elimination from the body, such as via controlled release formulations and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In alternative embodiments of the invention miRNA and antisense constructs such as antisense oligonucleotides may be administered to a subject in a vector. The vector may be a plasmid vector, a viral vector, or any other suitable vehicle adapted for the insertion and foreign sequences and introduction into eukaryotic cells. Preferably the vector is an expression vector capable of directing the transcription of the DNA sequence of an antisense molecule of the invention into RNA. Preferred viral expression vectors include for example epstein-barr virus-, bovine papilloma virus-, adenovirus- and adeno-associated virus-based vectors. In a particular embodiment, the vector is episomal. The use of a suitable episomal vector provides a means of maintaining the antisense molecule in the required target cells in high copy number extrachromosomally thereby eliminating potential effects of chromosomal integration.

In treating or preventing diseases and conditions, the present invention contemplates the administration of multiple miRNA and/or multiple miRNA antagonists. Whether it is suitable or desirable to administer one or more miRNA, one or more miRNA antagonists or optionally both miRNA and miRNA antagonists can be determined by those skilled in the art on a case-by-case basis. The invention also contemplates combination therapies, wherein agents as described herein are coadministered with other suitable agents which may facilitate the desired therapeutic or prophylactic outcome. For example, in the context of cancer, one may seek to maintain ongoing anti-cancer therapies such as chemotherapy and/or radiotherapy, in order to manage the condition of the patient, to improve local tumour control and/or reduce the risk of metastasis, whilst employing agents in accordance with embodiments of the present invention. By "coadministered" is meant simultaneous administration in the same formulation or in two different formulations via the same or different routes or sequential administration by the same or different routes. By "sequential" administration is meant a time difference of, for example, from seconds, minutes, hours, days, weeks or months between the administration of the two formulations or therapies. The formulations or therapies may be administered in any order.

The present invention also relates to the use of miRNAs disclosed herein for the diagnosis of, or determination of predisposition to, diseases and conditions associated with abnormal angiogenesis. Accordingly, an aspect of the invention provides a method for diagnosing a disease or condition associated with abnormal angiogenesis in a subject, or determining the predisposition of a subject to such a disease or condition, the method comprising:
(a) obtaining a biological sample from the subject; and
(b) determining the level of expression of at least one miRNA, or a precursor, derivative or variant thereof in the sample, the miRNA
  (i) comprising a seed region comprising the sequence UCACAGU (SEQ ID NO:37), or
  (ii) being selected from the group consisting of miR_27a, miR_27b, miR_24, miR_23a, miR_23b, miR_20a, miR_21, miR_29a, miR_29b, miR_29c, miR_106a, miR_126, miR_193a, miR_195, miR_197, miR_221, miR_347 and miR_126*,
wherein the level of expression of the at least one miRNA is indicative of a disease or condition associated with abnormal angiogenesis, or a predisposition thereto, in the subject.

miRNA and antagonists thereof as described herein may also be used for the screening and identification of molecules and compounds that interact with the miRNA disclosed herein, including endogenous nucleic acid and polypeptide targets of these miRNA. Such targets may be regulated by the miRNA, may regulate the miRNA and/or may exert an effect on other cellular molecules or processes involved in angiogenesis. Thus, such molecules and compounds may offer novel therapeutic targets. By "regulate" is meant regulation or modulation (either positive or negative) of activity or expression. Thus, for example, a molecule or compound may induce, promote, activate, increase, inhibit or prevent activity or expression of another molecule(s) or compound(s). Suitable molecules and compounds may exert their effect on by virtue of either a direct (for example binding) or indirect interaction. Molecules and compounds which bind, or otherwise interact with, miRNA disclosed herein may be identified by a variety of suitable methods known to those skilled in the art.

The present invention also provides kits for use in accordance with methods of the invention. For example, kits of the invention may contain oligonucleotides representing the miRNAs disclosed herein and/or antagonists thereof, such as antisense molecules specific for these miRNA. Such kits may be used, for example, to detect the presence of miRNAs in a biological sample and/or detect molecular targets or binding partners of such miRNA. Detection using such kits is useful for a variety of purposes, including but not limited to disease diagnosis, epidemiological studies and performing screening methods of the present invention. Additionally, kits may contain means for detecting the binding of an miRNA of the invention to a binding partner. For example oligonucleotides may be conjugated to a detectable substrate such as a fluorescent, radioactive or luminescent compound, enabling their detection in assays known to those skilled in the art. Kits according to the present invention may also include other components required to conduct the methods of the present invention, such as buffers and/or diluents. The kits typically include containers for housing the various components and instructions for using the kit components in the methods of the present invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

The following examples are illustrative of the invention and should not be construed as limiting in any way the general nature of the disclosure of the description throughout this specification.

Example 1

Regulation of miRNAs During Angiogenesis

Microarray analysis was conducted to determine patterns of expression of miRNA under angiogenic conditions in human umbilical vein endothelial cells (HUVECS). HUVECs were isolated by collagenase treatment as described in Gamble et al., 1993 (*J Cell Biol* 121:931-943). The cells were cultured in gelatin (Sigma) coated 25 cm² flasks in HUVEC medium (M199 with Earles Salts, 20 mM HEPES, 20% foetal calf serum (FCS; Cytosystems), sodium bicarbonate, 2 mM glutamine, nonessential amino acids, sodium pyruvate, fungizone, penicillin and streptomycin). Cells were grown at 37° C., 5% $CO_2$. HUVEC formed a confluent monolayer within two to four days and were then harvested by trypsin-EDTA treatment and transferred into a gelatin coated 75 cm² flask. Endothelial growth supplement (50 μg/ml, ECGS, Collaborative Research) and heparin (50 μg/ml, Sigma) were added. Cells were passaged (1:2 split) every three to four days and were used between passage two and four.

For induction an angiogenesis, HUVEC were harvested and either (i) lysed, (ii) stimulated with PMA and AC11 and lysed, or (iii) replated after PMA and AC11 stimulation onto a 3D collagen gel.

miRNA microarrays were performed as essentially as described in Thomson et al., 2004 (*Methods Enzymol* 427: 107-122). Briefly, RNA was extracted using Trizol (Invitrogen) and 5 ug labeled with 500 ng of Cy3 or Cy5 coupled dinucleotides (CU) in 1× Igloi buffer (0.1 mM ATP, 50 mM HEPES pH 7.8, 3.5 mM DTT, 20 mM $MgCl_2$, 10 mg/ml BSA, 10% DMSO) using 20 U T4 RNA ligase (NEB). Labeled RNA was resuspended in hybridization buffer (400 nM Na2HPo4, 0.8% BSA, 5.0% SDS, 13% formamide) and hybridized to microarrays spotted with probes to 377 miRNAs (Ambion mirVana™ miRNA Probe Set 1564V1). Competitive hybridsations were performed using RNA from two separate HUVEC cell line experiments with data from these biological replicates pooled for each time point. Arrays were scanned using a GenePix 4000B scanner driven by GenePix-Pro 4.0 (Molecular Devices). Analysis was performed using freely available statistical programming and graphics environment R (http://cran.r-project.org). miRNAs which were differentially expressed were identified using the empirical Bayes approach which ranks genes on a combination of magnitude and consistency of differential expression (Smyth, 2004, *Stat Appl Genet Mol Biol* 3:article 3).

FIG. 1A shows volcano plots of differentially regulated miRNAs at timepoints between 30 minutes and 24 hours post stimulation. Bayesian log odds of differential expression is plotted against log 2 (expression at timepoint divided by expression at time zero). A set of 18 miRNA were shown to be significantly downregulated, as listed in Table 2 below.

TABLE 2

| Differentially regulated miRNA | | | |
|---|---|---|---|
| miRNA | $A^1$ | $t^2$ | SEQ ID NO: |
| hsa_miR_27a | 10.76 | −24.09 | 1 |
| hsa_miR_27b | 9.327 | −31.61 | 2 |
| hsa_miR_24 | 11.62 | −9.765 | 3 |
| hsa_miR_23a | 11.15 | −10.38 | 4 |
| hsa_miR_23b | 10.62 | −18.43 | 5 |
| hsa_miR_20a | 10 | −15.73 | 6 |
| hsa_miR_21 | 9.317 | −36.25 | 7 |

TABLE 2-continued

| Differentially regulated miRNA | | | |
|---|---|---|---|
| miRNA | $A^1$ | $t^2$ | SEQ ID NO: |
| hsa_miR_29a | 9.769 | −28.74 | 8 |
| hsa_miR_29b | 11.23 | −21.49 | 9 |
| hsa_miR_29c | 9.223 | −19.09 | 10 |
| hsa_miR_106a | 10.56 | −7.238 | 11 |
| hsa_miR_126 | 11.06 | −20.89 | 12 |
| hsa_miR_193a | 9.953 | −14.48 | 13 |
| hsa_miR_195 | 9.424 | −17.54 | 14 |
| hsa_miR_197 | 9.467 | −11.93 | 15 |
| hsa_miR_221 | 10.12 | −15.16 | 16 |
| mo_miR_347 | 9.357 | −15.02 | 17 |
| hsa_miR_126* | 9.886 | −11.81 | 18 |

[1] A = intensity of the spot on the microarray
[2] t = probability value

Figure 1B:
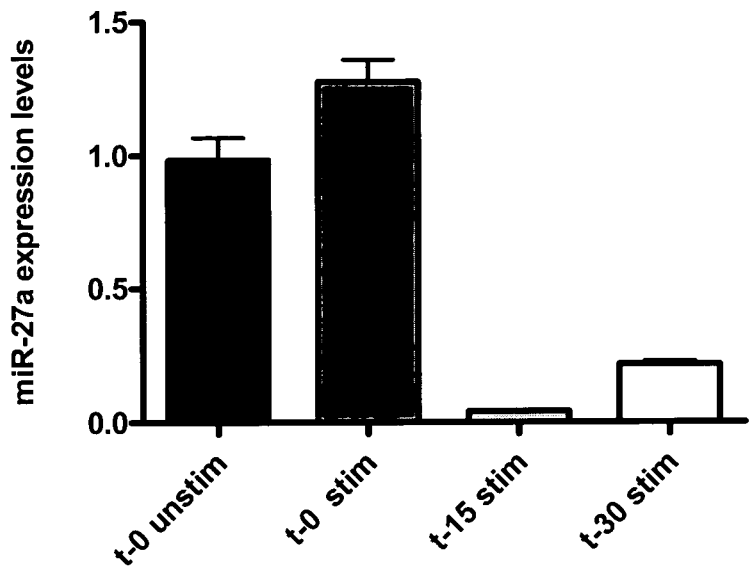
Figure 2:
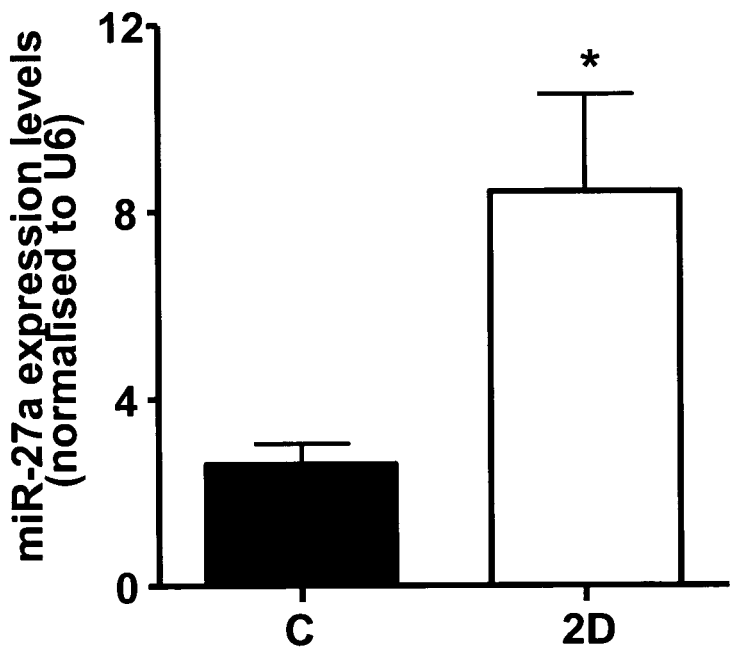
FIG. 2. hsa_miR_27a levels are significantly reduced in a three-dimensional cell culture milieu but not in corresponding two-dimensional culture conditions. HUVEC were treated with stimulators of angiogenesis and then plated onto collagen coated plates (2D). Control (C) was stimulated and then directly lysed with no replating. Pooled data from 3 independent lines of HUVECs with experiments performed on different days. *p=0.05. [For results of downregulation of hsa_miR_27a levels in a three-dimensional cell culture milieu refer to FIG. 1.]

Quantification of expression levels of one of these miRNA, hsa_miR_27a is shown in FIG. 1B. HUVEC were harvested and either lysed (t-0 unstim) or stimulated with PMA and AC11 and lysed (t-0 stim) or were replated after PMA and AC11 stimulation onto a 3D collagen gel for either 15 or 30 minutes. The downregulation of miR-27a expression was evident when compared to levels seen in cells that were detached but not stimulated or to levels in cells which were detached, stimulated but not plated onto the collagen gel. Surprisingly, as shown in FIG. 2, downregulation of expression levels of endogenous hsa_miR_27a are observed only in a differentiation-inducing angiogenic three-dimensional cell culture milieu rather than in a standard two-dimensional cell culture system under the same conditions.

Example 2

Overexpression of hsa_miR_27a Inhibits Vessel Formation

The effect of hsa_miR_27a expression on vessel formation was investigated in both in vitro and in vivo models of angiogenesis.

General Methods

Transfection with Pre-miR™ miRNA Precursor Molecules.

HUVEC were seeded at 6×10⁵ cells per 25 cm² flask and 24 h later were transfected with synthetic microRNAs (Pre-miR™ miRNA Precursor Molecules, Ambion) at a final concentration of 15 nM using HiPerFect transfection reagent (Qiagen). Total RNA and protein were collected at either 24 h or 48 h post transfection. HEK293 cells were seeded at 5×10⁴ cells in a 24-well plate and were transfected 24 h later with 50 ng of plasmid in addition to synthetic microRNA molecules at a final concentration of 15 nM. Cell lysates were made 24 h post transfection.

RNA Extraction and Real-Time PCR.

Total RNA was isolated from HUVEC by Trizol extraction (Invitrogen) according to the manufacturer's instructions. Isolated RNA was subsequently quantified using the Nano-Drop spectrophotometer at 260 nm. For mRNA analysis, in order to remove residual DNA from isolated RNA, DNase treatment (Sigma) was performed according to manufacturer's instructions. Complementary DNA (cDNA) was randomly primed from 1 ug of total RNA using the High Capacity cDNA Reverse Transcription Kit (Applied Biosystems). Real-time PCR was then carried out in triplicate with a 1:4 dilution of the cDNA, using the Green JumpStart™ Taq ReadyMix™ (Sigma) on a Rotorgene 6000 series PCR machine (Corbett Research). Analysis of data was performed using the software accompanying the PCR machine and data were normalized to β-actin. For analysis of miRNA expression, cDNA synthesis was performed using the TaqMan® MicroRNA Reverse Transcription Kit (Applied Biosystems) using TaqMan® MicroRNA assays according to the manufacturer's instructions (Applied Biosystems). MicroRNA data are expressed relative to small nuclear RNA U6 (snoU6).

Matrigel® Tube Formation Assay.

According to the manufacturers instructions, Matrigel® (Becton Dickinson) was thawed and 100 μl of Matrigel® was added to a flat bottom 96 well plate which was allowed to polymerize at 37° C. for 1 hour. HUVEC were then plated at $3.6 \times 10^4$ cells per well in HUVEC medium. Photographs were taken at regular intervals over 24 hours.

Permeability Assay.

The permeability assay was performed as previously described (Li et al., 2004, *Blood* 104:1716). Briefly, 24 h post transfection HUVEC were plated at $1 \times 10^5$ cells per transwell (Corning) for 24 hours in HUVEC medium and then in 2% FCS HUVEC medium for a further 24 hours. FITC-conjugated dextran (2 μg) was added to the upper chamber of all wells. The amount of FITC-dextran in the lower chambers of the transwells was determined using a LS 50B Luminescence Spectrometer (Perkin Elmer) at an excitation wavelength of 485 nm and emission wavelength of 530 nm. Permeability is given as the amount of FITC-dextran passing from the upper chamber to the lower chamber. HUVEC overexpressing miR-27a were plated on to transwells 24 hours after the transfection procedure and treated in the same manner as cells transfected with a pre-miR control.

Immunoblotting.

HUVEC were lysed in ice-cold lysis buffer (1M Tris.HCl, pH 7.5, with 1% NP-40, 5M NaCl, 200 mM EGTA, 500 mM NaF, 100 mM $Na_4P_2O_7$ and protease inhibitor cocktail). Protein concentrations were assayed using Bradford Reagent (BioRad). Equal amounts of protein were loaded onto an acrylamide gel, separated by SDS-PAGE, transferred to PVDF membrane, blocked with 5% skim milk powder in PBS, and probed with an appropriate primary and secondary antibody. After washing, reactive bands were detected by chemiluminescence (Amersham 8 Pharmacia Biotech). Membranes were washed and re-probed using a monoclonal anti-Beta actin antibody (Sigma) as a loading control.

Collagen Assay.

The capillary tube formation assay was performed as previously described (Gamble et al., 1993, *J Cell Biol* 121:931). Briefly, $6.4 \times 10^4$ cells/160 μl HUVEC medium were plated onto 100 μl gelled rat type I collagen (Becton Dickinson) in 96-well flat-bottomed microtiter plates. Capillary tube formation was stimulated by the addition of 20 ng/ml phorbol myristate acetate (PMA) and an antibody against α$\beta_1$-integrin (RMAC11), which promotes the formation of complex multicellular tubes.

Results

Figure 3:
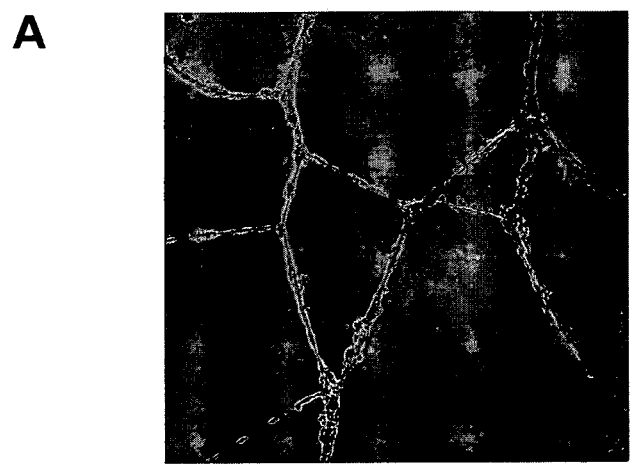
Figure 3:
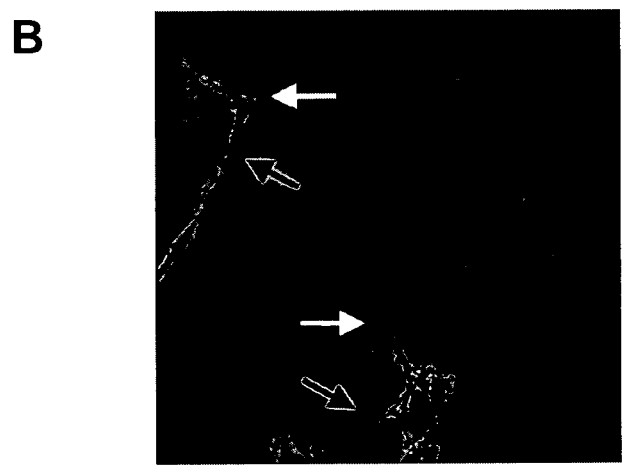
Figure 3:
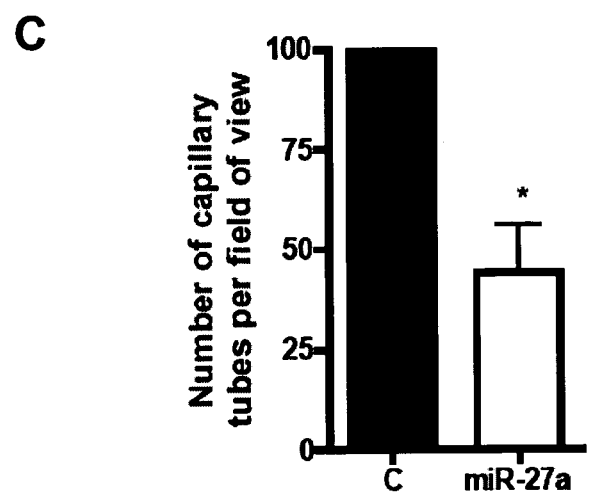

As shown in FIG. 3, overexpression of hsa_miR_27a disrupts in vitro tube formation. HUVEC were transfected with either a pre-miR negative control (FIG. 3A) or with a precursor for hsa_miR_27a which allowed its overexpression (FIG. 3B). Both control and miR_27a transfected cells were seen to realign within the first 6 hours as normal. However, the cells overexpressing miR_27a failed to extend and mature (FIG. 3B). By 12 hours, miR_27a overexpressing cells showed thin projections which often failed to join, tubes that had formed within this period were breaking apart and there was a significant decrease in the number of fully formed capillary tubes (FIG. 3C). These results indicate that the downregulation of miR_27a is necessary for stable capillary tube formation and maturation to occur.

Figure 4:
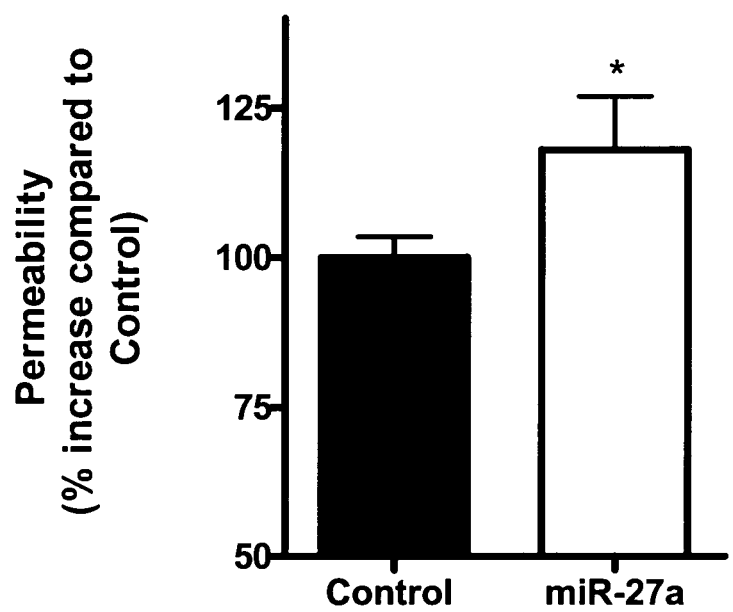
FIG. 4. Overexpression of hsa_miR_27a alters endothelial cell permeability. HUVEC were plated onto transwells 24 post transfection with either a pre-miRNA control or hsa_miR_27a precursor and permeability measured 24 hours later. Permeability is given as the amount of FITC-dextran passing from the upper to the lower chamber (normalized to the control). Results shown are the average of five independent HUVEC lines ±s.e.m. * Control vs miR-27a, T-test: $p<0.05$.

Further evidence of the effect of overexpression of hsa_miR_27a on tube formation can be seen in FIG. 4 illustrating increased endothelial cell permeability following transfection with hsa_miR_27a precursor suggesting an alteration in the configuration of the cell junctions.

Example 3 hsa_miR_27a Expression in Human Disease

The level of expression of hsa_miR_27a was determined in endothelial cells from human patients with hepatocellular carcinoma. Archival material of paraffin fixed liver samples from patients with hepatocellular carcinoma were obtained through the Liver Department of Royal Prince Alfred Hospital. Paraffin embedded liver sections were also obtained from three patients with cirrhosis. The fibrotic area surrounding the regenerative nodules is known to be a setting where neovessels are forming and this area in normal liver is free from such neo-vessels. Blood vessels were detected using PECAM expression. Excision of endothelial cells from the venule and neo-angiogenic vessels were achieved using the Arcturus PixCell Ile instrument. Extraction protocol was as recommended by the manufacturer. Laser diameter was set to 7.5 μM and laser pulse set at 0.2 seconds. Endothelial cells were transferred onto CapSure Macro LCM Caps which enables the precise and rapid extraction of populations of pure cells from venules and neo-vessels by laser capture microdissection (LCM). Approximately 5-10 LCM Caps were collected for the two endothelial cell populations. Images were acquired at room temperature using UPlanFI 4×/0.13, UPlanFI 10×/0.30, LCPlanFI 20×/0.40 objectives on a Arcturus PixCell Ile microscope (Molecular Devices) and acquired to a Hitachi ½ inch single chip CCD colour camera (Hitachi). Images were adjusted for brightness and contrast using LCM ver. 2.0 software.

Isolation of total RNA was achieved using TRIzol (Invitrogen) according to manufacturer's instructions. MiRNA analysis was performed using TaqMan Low Density Human Arrays (Applied Biosystems). Raw cycle threshold (Ct) values for each miRNA were obtained and mined for expression analysis. Levels of miR_27a were measured by Q-PCR.

Figure 5:
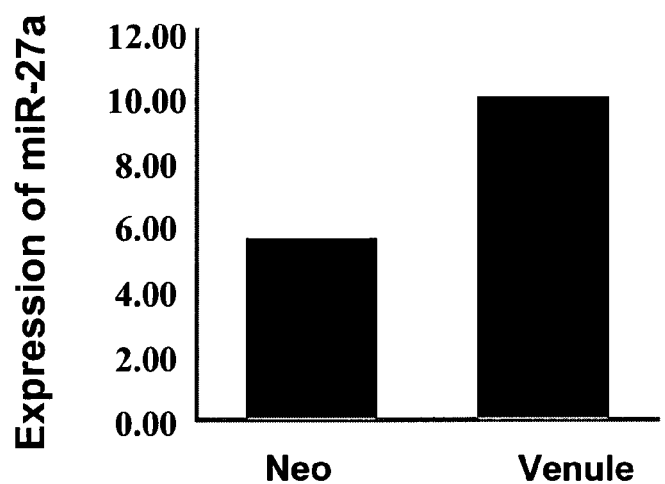
FIG. 5. (A) Expression of hsa_miR27a in neoangiogenic endothelial cells (neo) and endothelial cells from venules (venule), obtained from a human patient with hepatocellular carcinoma. Data expressed relative to mean Ct ($2^{\bar{x}}$ Ct). (B) RNA was isolated from endothelial cells in either venules or neo-angiogenic vessels (Neo) from cirrhosis patients (i, ii and iii). Expression levels of miR_27a were quantified by Q-PCR and normalized to miR-520d*. Data represents the mean of quadruplicate Q-PCR reactions ±SEM *, $p<0.05$ Venules vs Neo.
Figure 5:
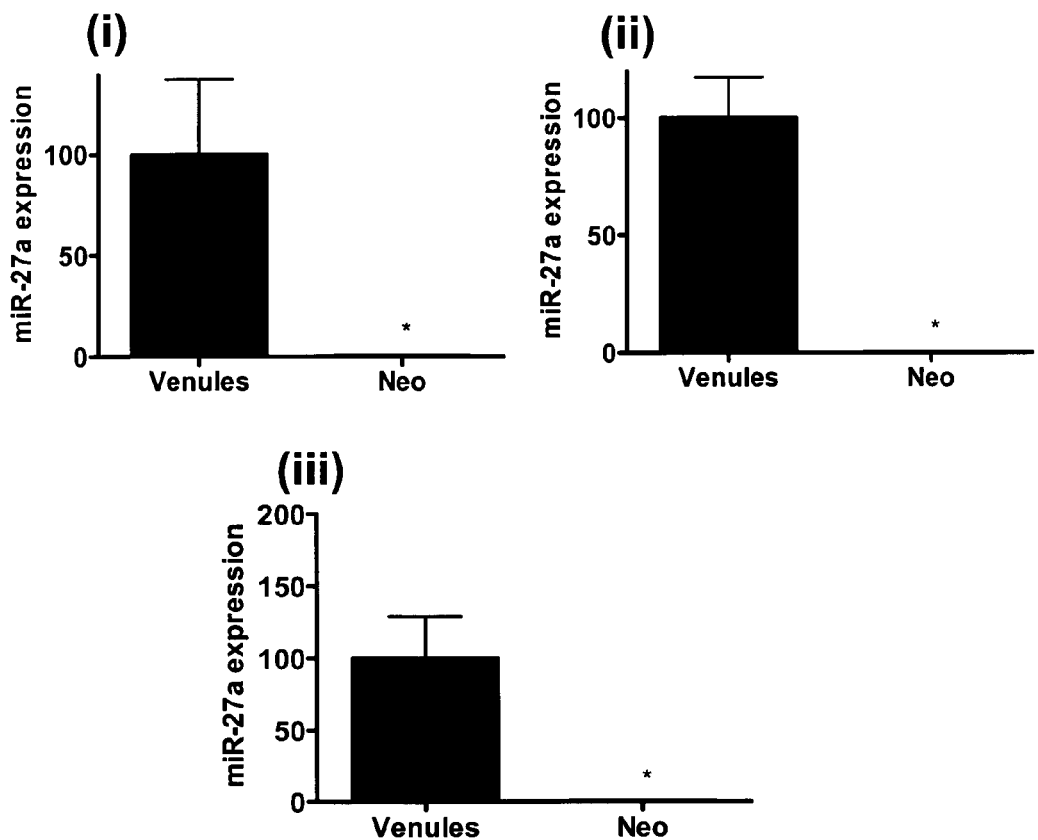

Data obtained using neoangiogenic endothelial cells and endothelial cells from venules from one hepatocellular carcinoma patient sample are shown in FIG. 5A. It can be seen that expression of miR_27a is reduced almost two-fold in the neoangiogenic cells when compared to venule cells. Similar results were obtained for a second hepatocellular carcinoma patient sample (data not shown). In liver sections from all three patients with cirrhosis there was a highly significant decrease in the expression of miR_27a in the neo-vessels when compared with venules (FIG. 5B). Results were normalized to miR-520d* (a miRNA confirmed not to be regulated between the two endothelial cell populations).

Example 4

Overexpression of miR_27a Reduces In Vivo Capillary Tube Formation

A murine Matrigel plug assay was used in order to confirm that miR_27a is critical for the regulation of angiogenesis in vivo.

The assay was performed as previously described (Zhang et al., 2006, *J Cell Sci* 119:3219). Six to eight week-old female C57BL/6 mice were injected subcutaneously (right flanks) with 500 ul of Matrigel containing FGF-2 (0.5 ug, (Sigma, Mich.), 90 ug control or miR-27a mimic, or no mimic, and FuGENE6 (2.5 ul). 14 days later, plugs were resected and fixed in 10% paraformaldehyde. 5 um cross-sections were stained with Haematoxylin-Eosin. Erythrocyte-containing vessels in the plugs were quantified by light microscopy under 100× magnification and expressed as the mean of three random fields. All animal experiments were approved by the University of New South Wales Animal Care and Ethics Committee. Images were acquired at room temperature using a UplanFI 20×/0.50 objective for panel A and UPIanFI 40×/0.77 objective for panel B on a BX51 microscope to a DP70 camera using DPC Controller 3.1.1.267 software (all from Olympus). Subsequent to data acquisition, ImageJ (NIH) was used to make luminosity and contrast adjustments.

Figure 6:
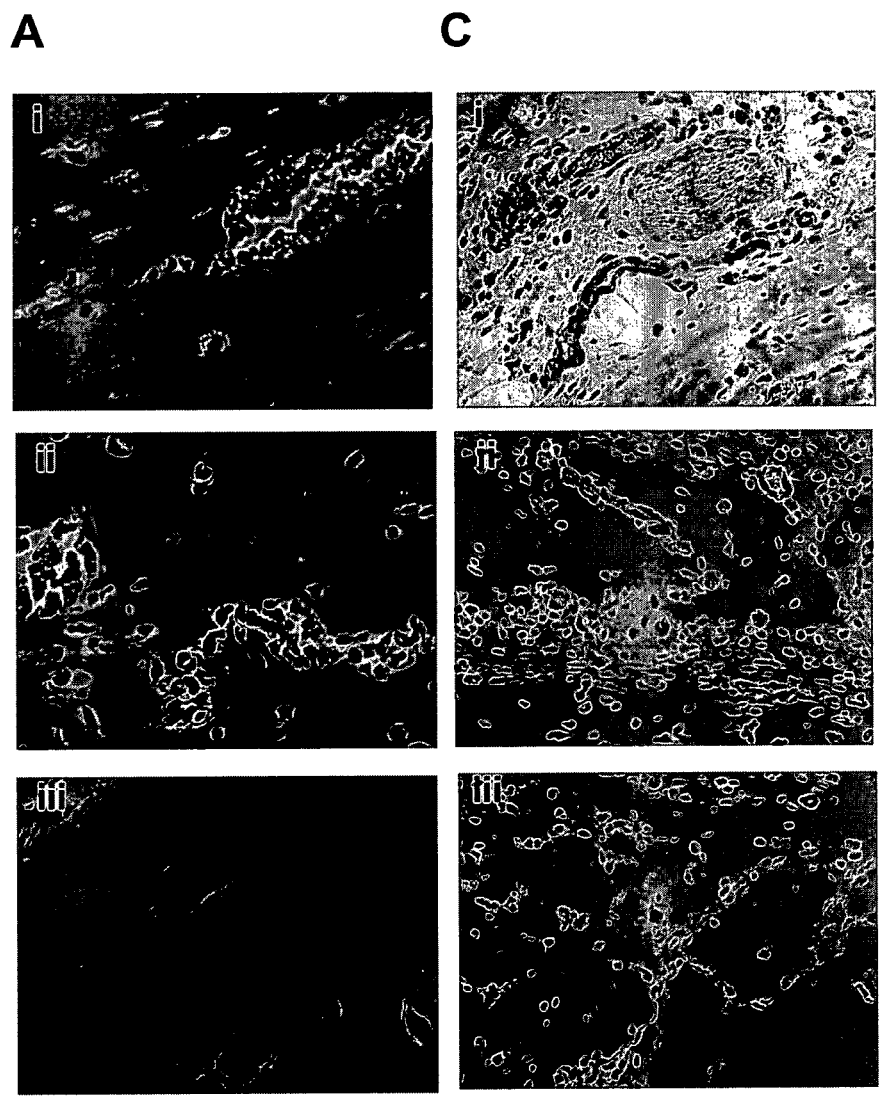
FIG. 6. Overexpression of miR_27a reduces in vivo capillary tube formation. C57BL/6 mice were implanted subcutaneously with Matrigel plugs containing 0.5 µg FGF-2 and either 90 µg control (C) or miR_27a mimic or vehicle only (V). (A) Representative histologic sections and hematoxylin and eosin stained cross-sections for vehicle (i), control (ii) and miR_27a (iii). Scale bar: 20 µm. (B) Number of erythrocyte containing vessels quantified. Data is expressed as mean±SEM. (C) Representative CD31 immunochemistry from the Matrigel plug. Scale bar: 50 µm. (D) Number of CD31 positive cells quantified. Data is expressed as mean±SEM. Statistical analysis of differences was compared by one-way ANOVA with Bonferroni's correction for multiple comparisons. For control n=3 mice and for miR_27a and vehicle n=6 mice. Experiments were carried out on two separate days using two separate batches of miRNA mimics.

Hematoxylin and eosin stained cross-sections from the Matrigel/skin interface showed erythrocyte-containing vessels or sprouting mature vessels. Induced stromal development, cell infiltration, and capillary luminal blood vessels were visible in the controls but not to the same extent in the miR_27a implant (FIGS. 6A and B). Furthermore, this significant reduction in the number of vessels was also detectable when the sections were stained for CD31 (PECAM) (FIGS. 6C and 7D). Thus, miR_27a overexpression inhibits blood vessel invasion into the Matrigel plug suggesting that miR_27a is anti-angiogenic.

Example 5

Effect of miR_27a on VE-Cadherin Expression

Using web-based target prediction algorithms including TargetScan, PicTar and miR_27a was predicted to target VE-cadherin, the endothelial specific, calcium-dependent cell adhesion molecule, responsible for cell-cell interactions and adhesion in solid tissues. The 3'UTR of VE-cadherin contains a single predicted 8-mer site for miR-27 with an exact match at positions 2-8 of the mature miRNA followed by an 'A' (the seed region+position 8).

To determine whether miR_27 regulates VE-cadherin expression, the protein levels of VE-cadherin were measured in miR_27a overexpressing cells. For these experiments, HUVEC were seeded at $4 \times 10^5$ cells per 25 $cm^2$ flask and 24 h later were transfected with microRNAs mimics (Pre-miR™ miRNA Precursor Molecules, Ambion) or LNA (Exiqon) at a final concentration of 15 nM using HiPerFect transfection reagent (Qiagen). In five independent HUVEC lines tested, there was a significant decrease (25%+/−4%) in VE-cadherin protein expression at 48 hours post transfection. Increasing the dose of miRNA mimic did not significantly alter the effects on VE-cadherin observed (data not shown). The level of VE-cadherin mRNA was measured using Q-PCR. There was a decrease (31%+/−7%) in the mRNA levels of VE-cadherin seen in the miR_27a overexpressing cells in five independent HUVEC lines tested. Conversely, knockdown of miR_27a using locked nucleic acid (LNA) based technology showed an upregulation (22%+/−4%, n=2) of VE-cadherin at the protein level.

Further experiments using luciferase reporter constructs generated encoding the wild-type 3'UTR of VE-cadherin or where the miR_27a site was mutated showed that miR_27a has the capacity to regulate VE-cadherin expression through direct binding to the 3'UTR of VE-cadherin. There was a significant repression of luciferase activity (33%+/−3%) in cells transfected with construct containing the wild type 3'UTR plus miR-27a mimic, when compared with the wild type 3'UTR plus the control mimic. Mutation of the miRNA site was able to reverse the repression of luciferase activity (data not shown). Furthermore, overexpression or knockdown of miR-27a was shown to cause a significant redistribution of VE-cadherin within the cell (data not shown).

The invention claimed is:

1. A method for promoting or inducing angiogenesis in cells or tissue of a subject, the method comprising:
   selecting a subject in need of the promotion or induction of angiogenesis; and administering to the subject, or cells or tissue derived therefrom, one or more antagonists of a miRNA, wherein;
   said miRNA is miR-27a; and
   said antagonist is an antisense oligonucleotide specific for miR-27a.

2. The method of claim 1 wherein the miR_27a is hsa miR_27a and comprises the nucleotide sequence set forth in SEQ ID NO:1.

3. The method of claim 1 wherein the antisense oligonucleotide comprises a nucleotide sequence as set forth in SEQ ID NO:19.

4. The method of claim 1 wherein the oligonucleotide sequence comprises one or more modifications such as non-naturally occurring nucleotide analogues, non-phosphate linkages between nucleotides, and/or conjugated moieties.

5. The method of claim 1 wherein the promotion or inducement of angiogenesis is for wound repair.

6. The method of claim 1 wherein the promotion or inducement of angiogenesis is for tissue repair, tissue regeneration or tissue engineering.

7. The method of claim 1 wherein the subject suffers from, is predisposed to, or otherwise at risk of developing a condition, associated with impaired or suppressed angiogenesis.

8. The method of claim 7 wherein the condition is coronary artery disease, stroke, a gynaecological disorder, infertility, or an ischemic wound.

9. The method of claim 5, wherein the wound repair is the healing of ischemic wounds.

* * * * *

SEQUENCE LISTING

```
<160> NUMBER OF SEQ ID NOS: 37

<210> SEQ ID NO 1
<211> LENGTH: 21
<212> TYPE: RNA
<213> ORGANISM: Homo sapiens

<400> SEQUENCE: 1
uucacagugg cuaaguuccg c                                              21

<210> SEQ ID NO 2
<211> LENGTH: 21
<212> TYPE: RNA
<213> ORGANISM: Homo sapiens

<400> SEQUENCE: 2
uucacagugg cuaaguucug c                                              21

<210> SEQ ID NO 3
<211> LENGTH: 23
<212> TYPE: RNA
<213> ORGANISM: Homo sapiens

<400> SEQUENCE: 3
gugccuacug agcugauauc agu                                            23
```

```
<210> SEQ ID NO 4
<211> LENGTH: 21
<212> TYPE: RNA
<213> ORGANISM: Homo sapiens

<400> SEQUENCE: 4
aucacauugc caggggauuuc c                                              21

<210> SEQ ID NO 5
<211> LENGTH: 21
<212> TYPE: RNA
<213> ORGANISM: Homo sapiens

<400> SEQUENCE: 5
aucacauugc caggggauuac c                                              21

<210> SEQ ID NO 6
<211> LENGTH: 23
<212> TYPE: RNA
<213> ORGANISM: Homo sapiens

<400> SEQUENCE: 6
uaaagugcuu auagugcagg uag                                             23

<210> SEQ ID NO 7
<211> LENGTH: 22
<212> TYPE: RNA
<213> ORGANISM: Homo sapiens

<400> SEQUENCE: 7
uagcuuauca gacugauguu ga                                              22

<210> SEQ ID NO 8
<211> LENGTH: 21
<212> TYPE: RNA
<213> ORGANISM: Homo sapiens

<400> SEQUENCE: 8
uagcaccauc ugaaaucggu u                                               21

<210> SEQ ID NO 9
<211> LENGTH: 23
<212> TYPE: RNA
<213> ORGANISM: Homo sapiens

<400> SEQUENCE: 9
uagcaccauu ugaaaucagu guu                                             23

<210> SEQ ID NO 10
<211> LENGTH: 22
<212> TYPE: RNA
<213> ORGANISM: Homo sapiens

<400> SEQUENCE: 10
uagcaccauu ugaaaucggu ua                                              22

<210> SEQ ID NO 11
<211> LENGTH: 23
<212> TYPE: RNA
<213> ORGANISM: Homo sapiens

<400> SEQUENCE: 11
aaaagugcuu acagugcagg uag                                             23
```

```
<210> SEQ ID NO 12
<211> LENGTH: 21
<212> TYPE: RNA
<213> ORGANISM: Homo sapiens

<400> SEQUENCE: 12
ucguaccgug aguaauaaug c                                              21

<210> SEQ ID NO 13
<211> LENGTH: 22
<212> TYPE: RNA
<213> ORGANISM: Homo sapiens

<400> SEQUENCE: 13
aacuggccua caaagucccc gu                                             22

<210> SEQ ID NO 14
<211> LENGTH: 21
<212> TYPE: RNA
<213> ORGANISM: Homo sapiens

<400> SEQUENCE: 14
uagcagcaca gaaauauugg c                                              21

<210> SEQ ID NO 15
<211> LENGTH: 22
<212> TYPE: RNA
<213> ORGANISM: Homo sapiens

<400> SEQUENCE: 15
uucaccaccu ucuccaccca gc                                             22

<210> SEQ ID NO 16
<211> LENGTH: 23
<212> TYPE: RNA
<213> ORGANISM: Homo sapiens

<400> SEQUENCE: 16
agcuacauug ucugcugggu uuc                                            23

<210> SEQ ID NO 17
<211> LENGTH: 19
<212> TYPE: RNA
<213> ORGANISM: Rattus norvegicus

<400> SEQUENCE: 17
ugucccucug ggucgccca                                                 19

<210> SEQ ID NO 18
<211> LENGTH: 21
<212> TYPE: RNA
<213> ORGANISM: Homo sapiens

<400> SEQUENCE: 18
cauuauuacu uuugguacgc g                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetic construct

<400> SEQUENCE: 19
```

```
gcggaacuua gccacuguga a                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic Construct

<400> SEQUENCE: 20
gcagaacuua gccacuguga a                                              21

<210> SEQ ID NO 21
<211> LENGTH: 23
<212> TYPE: RNA
<213> ORGANISM: Artificial Sequence
<220> FEATURE:
<223> OTHER INFORMATION: Synthetic Construct

<400> SEQUENCE: 21
acugauauca gcucaguagg cac                                            23

<210> SEQ ID NO 22
<211> LENGTH: 21
<212> TYPE: RNA
<213> ORGANISM: Artificial Sequence
<220> FEATURE:
<223> OTHER INFORMATION: Synthetic construct

<400> SEQUENCE: 22 ggaaucccu ggcaauguga u                                               21

<210> SEQ ID NO 23
<211> LENGTH: 21
<212> TYPE: RNA
<213> ORGANISM: Artificial Sequence
<220> FEATURE:
<223> OTHER INFORMATION: Synthetic construct

<400> SEQUENCE: 23
gguaaucccu ggcaauguga u                                              21

<210> SEQ ID NO 24
<211> LENGTH: 23
<212> TYPE: RNA
<213> ORGANISM: Artificial Sequence
<220> FEATURE:
<223> OTHER INFORMATION: Synthetic construct

<400> SEQUENCE: 24
cuaccugcac uauaagcacu uua                                            23

<210> SEQ ID NO 25
<211> LENGTH: 22
<212> TYPE: RNA
<213> ORGANISM: Artificial Sequence
<220> FEATURE:
<223> OTHER INFORMATION: Synthetic construct

<400> SEQUENCE: 25
ucaacaucag ucugauaagc ua                                             22

<210> SEQ ID NO 26
<211> LENGTH: 21
<212> TYPE: RNA
```

<213> ORGANISM: Artificial Sequence
<220> FEATURE:
<223> OTHER INFORMATION: Synthetic construct

<400> SEQUENCE: 26
aaccgauuuc agauggugcu a          21

<210> SEQ ID NO 27
<211> LENGTH: 23
<212> TYPE: RNA
<213> ORGANISM: Artificial Sequence
<220> FEATURE:
<223> OTHER INFORMATION: Synthetic construct

<400> SEQUENCE: 27
aacacugauu ucaaauggug cua          23

<210> SEQ ID NO 28
<211> LENGTH: 22
<212> TYPE: RNA
<213> ORGANISM: Artificial Sequence
<220> FEATURE:
<223> OTHER INFORMATION: Synthetic construct

<400> SEQUENCE: 28
uaaccgauuu caaauggugc ua          22

<210> SEQ ID NO 29
<211> LENGTH: 23
<212> TYPE: RNA
<213> ORGANISM: Artificial Sequence
<220> FEATURE:
<223> OTHER INFORMATION: Synthetic construct

<400> SEQUENCE: 29
cuaccugcac uguaagcacu uuu          23

<210> SEQ ID NO 30
<211> LENGTH: 21
<212> TYPE: RNA
<213> ORGANISM: Artificial Sequence
<220> FEATURE:
<223> OTHER INFORMATION: Synthetic construct

<400> SEQUENCE: 30
gcauuauuac ucacgguacg a          21

<210> SEQ ID NO 31
<211> LENGTH: 22
<212> TYPE: RNA
<213> ORGANISM: Artificial Sequence
<220> FEATURE:
<223> OTHER INFORMATION: Synthetic construct

<400> SEQUENCE: 31
acugggacuu uguaggccag uu          22

```
<210> SEQ ID NO 32
<211> LENGTH: 21
<212> TYPE: RNA
<213> ORGANISM: Artificial Sequence
<220> FEATURE:
<223> OTHER INFORMATION: Synthetic construct

<400> SEQUENCE: 32
gccaauauuu cugugcugcu a                                              21

<210> SEQ ID NO 33
<211> LENGTH: 22
<212> TYPE: RNA
<213> ORGANISM: Artificial Sequence
<220> FEATURE:
<223> OTHER INFORMATION: Synthetic construct

<400> SEQUENCE: 33
gcugggugga gaagguggug aa                                             22

<210> SEQ ID NO 34
<211> LENGTH: 23
<212> TYPE: RNA
<213> ORGANISM: Artificial Sequence
<220> FEATURE:
<223> OTHER INFORMATION: Synthetic construct

<400> SEQUENCE: 34
gaaacccagc agacaaugua gcu                                            23

<210> SEQ ID NO 35
<211> LENGTH: 19
<212> TYPE: RNA
<213> ORGANISM: Artificial Sequence
<220> FEATURE:
<223> OTHER INFORMATION: Synthetic construct

<400> SEQUENCE: 35
ugggcgaccc agagggaca                                                 19

<210> SEQ ID NO 36
<211> LENGTH: 21
<212> TYPE: RNA
<213> ORGANISM: Artificial Sequence
<220> FEATURE:
<223> OTHER INFORMATION: Synthetic construct

<400> SEQUENCE: 36
cgcguaccaa aaguaauaau g                                              21

<210> SEQ ID NO 37
<211> LENGTH: 7
<212> TYPE: RNA
<213> ORGANISM: Homo sapiens

<400> SEQUENCE: 37 ucacagu                                                               7
```